United States Patent
Newsome et al.

(10) Patent No.: US 6,586,611 B1
(45) Date of Patent: Jul. 1, 2003

(54) ZINC-MONOCYSTEINE COMPLEX AND METHOD OF USING ZINC-CYSTEINE COMPLEXES

(76) Inventors: David A. Newsome, 1701 Oriole, New Orleans, LA (US) 70122; David Tate, 5100 Marigny, New Orleans, LA (US) 70122

( * ) Notice: Subject to any disclaimer, the term of this patent is extended or adjusted under 35 U.S.C. 154(b) by 0 days.

(21) Appl. No.: 09/756,152

(22) Filed: Jan. 8, 2001

Related U.S. Application Data

(60) Provisional application No. 60/174,960, filed on Jan. 7, 2000.

(51) Int. Cl.[7] .......................... C07F 3/06; A61K 31/315
(52) U.S. Cl. ........................................ 556/134; 514/494
(58) Field of Search ........................... 556/134; 514/494

(56) References Cited

U.S. PATENT DOCUMENTS 5,911,978 A * 6/1999 Carr et al. ................. 424/70.1

OTHER PUBLICATIONS

Shindo et al., Journal of the American Chemical Society, vol. 87, No. 9, pp. 1904–1909 (May 5, 1965).*

* cited by examiner

*Primary Examiner*—Porfirio Nazario-Gonzalez
(74) *Attorney, Agent, or Firm*—Garvey, Smith, Nehrbass & Doody, L.L.C.; Seth M. Nehrbass

(57) ABSTRACT

A method of providing zinc to a subject in need of treatment includes administering to the subject an effective amount of a zinc-cysteine complex. The zinc-cysteine complex is preferably a zinc-monocysteine complex. The complexes of zinc-cysteine of the present invention increase the activity of antioxidant enzymes catalase and glutathione peroxidase, and the antioxidant protein metallothionein. The complexes of zinc-cysteine of the present invention protect retinal pigment epithelial cells from increasing hydrogen peroxide concentrations.

16 Claims, No Drawings

ZINC-MONOCYSTEINE COMPLEX AND METHOD OF USING ZINC-CYSTEINE COMPLEXES

CROSS-REFERENCE TO RELATED APPLICATIONS

Priority of U.S. Provisional Patent Application Serial No. 60/174,960, filed Jan. 7, 2000, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to nutritional supplements. More particularly, the present invention relates to nutritional supplements providing zinc to a subject in need of treatment.

2. General Background of the Invention

Zinc, an essential nutrient, is the second most abundant trace element in the human body and the most abundant trace element in the eye. It is necessary for the activity of more than 200 enzymes and for the DNA binding capacity of over 400 nuclear regulatory elements. There is evidence that zinc may function as an antioxidant by protecting sulfhydryl groups from oxidation, competing with copper and iron to reduce the formation of hydroxyl radicals which are a result of redox cycling and by the induction of the antioxidant protein metallothionein (MT) which can scavenge damaging hydroxyls.

It has been suggested that oxidative stress and a decrease in antioxidant capacity play a role in several pathological conditions such as atherosclerosis, carcinogenesis, and macular degeneration. Age-related macular degeneration (AMD) is the number one cause of blindness in people over 60 in the United States. It is thought that it is an age-related defect in the retinal pigment epithelium (RPE) which contributes to this disease, however, the etiology is unknown and currently there is no cure. Our laboratory has previously reported that the antioxidants catalase, MT, and zinc decrease with age and signs of age-related macular degeneration in isolated human retinal pigment epithelial cells.

Zinc has been implicated in beneficial effects on certain prostate conditions and functions, immune system function, and cancer.

Cysteine is a non-essential amino acid necessary for the formation of sulfur containing compounds such as pyruvate, taurine, and glutathione, important in normal tissue metabolism protection and repair.

Synthesis of glutathione is largely regulated by cysteine availability. An increase in glutathione levels are beneficial when the body encounters toxic conditions such as peroxide formation, ionizing radiation, alkylating agents, or other reactive intermediates.

In premature infants, cysteine levels are low, thereby making them more susceptible to oxidative damage of hydroperoxides formed in the eye after hyperbaric oxygen treatments.

The following U.S. Patents are incorporated herein by reference:

U.S. Pat. No. 5,844,089 Genetically fused globin-like polypeptides having hemoglobin-like activity U.S. Pat. No. 5,844,088 Hemoglobin-like protein comprising genetically fused globin-like polypeptides U.S. Pat. No. 5,801,019 DNA encoding fused alpha-beta globin pseuodimer and production of pseudotetrameric hemoglobin U.S. Pat. No. 5,798,227 Co-expression of alpha and beta globins U.S. Pat. No. 5,744,329 DNA encoding fused di-beta globins and production of pseudotetrameric hemoglobin U.S. Pat. No. 5,739,011 DNA for the production of multimeric hemoglobins U.S. Pat. No. 5,599,907 Production and use of multimeric hemoglobins U.S. Pat. No. 5,545,727 DNA encoding fused di-alpha globins and production of pseudotetrameric hemoglobin U.S. Pat. No. 5,401,770 Antipruritic agents and antipruritic compositions thereof U.S. Pat. Nos. 3,941,818; 4,021,569; 4,764,633.

U.S. Pat. No. 5,401,770 discloses the use of a zinc-cysteine complex in an external use antipruritic agent.

BRIEF SUMMARY OF THE INVENTION

The apparatus of the present invention solves the problems confronted in the art in a simple and straightforward manner. What is provided is a zinc-monocysteine complex and method of using zinc-cysteine complexes (and preferably zinc-monocysteine complexes) to provide zinc to subjects in need of treatment.

The present invention also includes a zinc-monocysteine complex, formed by the following method:

heating a 1:2 gram ratio of L-cysteine and Zn (metal) at about 85 degrees C. for about 2 hours; any solid residues were removed by filtration;

evaporating to dryness. The zinc-monocysteine complex so formed comprises $C_3H_5NSO_2Zn$.

The zinc-cysteine complex can be administered orally, and the amount administered is preferably 15–45 mg bioavailable zinc. The complex of zinc-cysteine increases the activity of antioxidant enzymes catalase and glutathione peroxidase, and the antioxidant protein metallothionein. The complex of zinc-cysteine protects retinal pigment epithelial cells from increasing hydrogen peroxide concentrations.

The present invention also comprises a method of providing cysteine to a subject in need of treatment comprising administering to the subject an effective amount of a zinc-cysteine complex. The zinc-cysteine complex can be a zinc-monocysteine complex, and it can be administered orally.

DETAILED DESCRIPTION OF THE INVENTION

Formulation of a zinc-cysteine complex may be beneficial in supplying the diet with two potent antioxidants and precursors for the formation of other antioxidant components.

EXAMPLE 1

A zinc-monocysteine complex was formed by the following method:

L-cysteine (50 g, 100 mmol) was dissolved in water and 100 g of zinc (metal) was added. The mixture was heated to 85 degrees C. for 2 hours. The mixture was filtered to remove unreacted solid residue. The mixture was then placed in an ethanol dry ice bath and evaporated to dryness.

The present inventors believe that they are the first to use zinc metal (as opposed to zinc salts) to form a zinc-cysteine complex.

The present inventors believe that they are the first to provide scientific evidence, that is, physical chemical evidence, that their method has produced a true zinc-monocysteine molecule.

The zinc-monocysteine complex so formed had the following formula: $C_3H_5NSO_2Zn$. It can be diagrammed as follows:

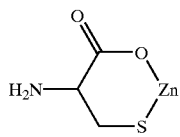

The L-cysteine and zinc combined in a ratio of 1:1 (L-cysteine:Zn).

The zinc-monocysteine complex so formed was tested in the following experiment:

The sample was analyzed by mass spectroscopy, nuclear magnetic resonance spectroscopy and elemental analysis. Results show the mass spectroscopy analysis is 186; the nuclear magnetic resonance spectroscopy analysis is 2.97 (2H, q-d, $CH_2$), 5.9 (1H, O, CH); elemental analysis revealed a 1:1 ratio of zinc to cysteine.

The biological efficacy was tested by adding 0, 15, 30 or 100 μM of zinc cysteine to cultured retinal pigment epithelial cells in comparison to zinc salts (zinc acetate, zinc chloride, and zinc sulfate).

The complex of zinc-cysteine increased the activity of antioxidant enzymes catalase and glutathione peroxidase, and the antioxidant protein metallothionein in cultured retinal pigment epithelial cells more efficiently and potently than zinc acetate, zinc chloride, and zinc sulfate. It was also more potent in protecting RPE cells from increasing hydrogen peroxide concentrations than were the zinc salts. The addition of cysteine alone did not have an effect on catalase or metallothionein levels. The zinc-cysteine complex maybe readily absorbed and distributed inside the cell to provide beneficial needs in regulating the antioxidant economy.

Dosage:
15–45 mg bioavailable zinc.
Methods of administration:
preferably oral, perhaps topical, and possibly intravenously.

EXAMPLE 2

A second (preferred) example is disclosed in the paper attached to the present patent application as filed, entitled "Preparation and Analysis of a Zinc cysteine Compound", and incorporated herein by reference. In this example, preparation of the zinc-monocysteine complex occurs as follows:

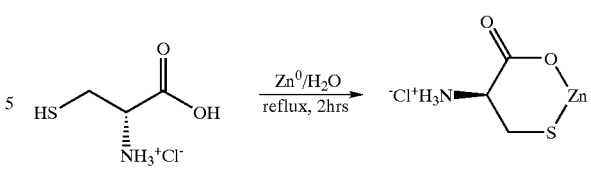

L-cysteine hydrochloride (50 g) was dissolved in water (200 ml; a 100 mmol solution) and zinc metal (130 g; 2 mol) was added. The reaction Mixture was slowly heated to 85 degrees C. over 15 minutes and stirred on a heated mixing plate for an additional 2 hours. The mixture was filtered and the solid residue discarded (136.87 g). The mixture was then placed in an ethanol dry ice bath and evaporated to solid residue (41.65 g; 84% recovery). This method produces a zinc-monocysteine complex.

Dosage and methods of administration for Example 2 can be as in Example 1.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. A zinc-monocysteine complex, comprising $ClC_3H_5NSO_2Zn$.

2. A method of providing zinc to a subject in need of treatment for deficiency of zinc comprising administering to the subject an effective amount of a zinc-cysteine complex comprising $ClC_3H_5NSO_2Zn$.

3. The method of claim 2, wherein the zinc-cysteine complex is a zinc-monocysteine complex.

4. A method of providing zinc to a subject in need of treatment for deficiency of zinc comprising orally administering to the subject an effective amount of a zinc-cysteine complex.

5. The method of claim 2, wherein the amount of zinc-cysteine complex administered contains 15–45 mg bioavailable zinc.

6. A method of providing zinc to a subject in need of treatment for deficiency of zinc comprising administering to the subject an effective amount of a zinc-cysteine complex comprising $ClC_3H_5NSO_2Zn$, wherein the complex of zinc-cysteine increases the activity of antioxidant enzymes catalase and glutathione peroxidase, and the antioxidant protein metallothionein.

7. A method of providing zinc to a subject in need of treatment for deficiency of zinc comprising administering to the subject an effective amount of a zinc-cysteine complex comprising $ClC_3H_5NSO_2Zn$, wherein the complex of zinc-cysteine protects retinal pigment epithelial cells from increasing hydrogen peroxide concentrations.

8. A zinc-cysteine complex suitable for oral ingestion by a human subject, comprising $ClC_3H_5NSO_2Zn$.

9. A zinc-monocysteine complex, comprising the zinc-cysteine complex shown in the equation below:

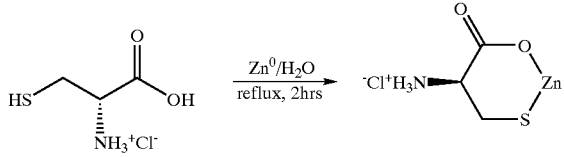

10. A method of providing cysteine to a subject in need of treatment for deficiency of cysteine comprising administering to the subject an effective amount of a zinc-cysteine complex comprising $ClC_3H_5NSO_2Zn$.

11. The method of claim 10, wherein the zinc-cysteine complex is a zinc-monocysteine complex.

12. A method of providing cysteine to a subject in need of treatment for deficiency of cysteine comprising orally administering to the subject an effective amount of a zinc-monocysteine complex.

13. The method of claim 10, wherein the amount of zinc-cysteine complex administered contains 15–45 mg bioavailable zinc.

14. A method of providing cysteine to a subject in need of treatment for deficiency of cysteine comprising administering to the subject an effective amount of a zinc-cysteine complex comprising $ClC_3H_5NSO_2Zn$, wherein the complex of zinc-cysteine increases the activity of antioxidant enzymes catalase and glutathione peroxidase, and the antioxidant protein metallothionein.

15. A method of providing cysteine to a subject in need of treatment for deficiency of cysteine comprising administering to the subject an effective amount of a zinc-cysteine complex comprising $ClC_3H_5NSO_2Zn$, wherein the complex of zinc-cysteine protects retinal pigment epithelial cells from increasing hydrogen peroxide concentrations.

16. The method of claim 10, wherein the zinc-cysteine complex is a zinc-monocysteine molecule.

* * * * *